United States Patent
Bogin et al.

(10) Patent No.: US 10,485,825 B2
(45) Date of Patent: Nov. 26, 2019

(54) PREVENTION OF PREGNANCY COMPLICATIONS BY NOBLE GAS ADMINISTRATION

(71) Applicant: NOBLIS THERAPEUTICS, INC., Portland, OR (US)

(72) Inventors: Vlad Bogin, Portland, OR (US); Thomas Ichim, San Diego, CA (US)

(73) Assignee: Nobilis Therapeutics, Inc., Portland, OR (US)

( * ) Notice: Subject to any disclaimer, the term of this patent is extended or adjusted under 35 U.S.C. 154(b) by 0 days.

(21) Appl. No.: 15/690,020

(22) Filed: Aug. 29, 2017

(65) Prior Publication Data

US 2018/0055876 A1    Mar. 1, 2018

Related U.S. Application Data

(60) Provisional application No. 62/380,903, filed on Aug. 29, 2016.

(51) Int. Cl.
| | | |
|---|---|---|
| *A01N 25/32* | (2006.01) | |
| *A61K 33/00* | (2006.01) | |
| *A61K 9/00* | (2006.01) | |

(52) U.S. Cl.
CPC ............ *A61K 33/00* (2013.01); *A61K 9/0043* (2013.01); *A61K 9/0073* (2013.01)

(58) Field of Classification Search
None
See application file for complete search history.

(56) References Cited

U.S. PATENT DOCUMENTS

| | | | | |
|---|---|---|---|---|
| 6,559,190 B1 | * | 5/2003 | Petzelt | A61K 33/00 514/771 |
| 2008/0187605 A1 | * | 8/2008 | Olney | A61K 31/045 424/600 |
| 2017/0020930 A1 | * | 1/2017 | Ichim | A61K 35/744 |
| 2017/0341980 A1 | * | 11/2017 | Bogin | C01B 21/24 |

FOREIGN PATENT DOCUMENTS

RU        002324486 C2  *  5/2008

* cited by examiner

*Primary Examiner* — Susan T Tran
(74) *Attorney, Agent, or Firm* — Baumgartner Patent Law; Marc Baumgartner

(57) ABSTRACT

Disclosed are means of preventing, reducing and/or treating pregnancy associated complications by administration of Noble Gas mixtures, directly by inhalation, or by other means of direct or indirect introduction, with the intended effect of reducing immunological/inflammatory events associated with said complications. In one embodiment the invention teaches the modulation of the maternal-fetal unit from a Th1/Th17 predisposition towards a Th2/Treg environment by inhalation of a combination of 30% xenon gas admixed with air, or combinations of medical grade oxygen and nitrogen.

11 Claims, No Drawings

PREVENTION OF PREGNANCY COMPLICATIONS BY NOBLE GAS ADMINISTRATION

CROSS-REFERENCE TO RELATED APPLICATIONS

This application claims priority to U.S. Provisional Application No. 62/380,903, filed Aug. 29, 2016, which is incorporated herein by reference in its entirety

FIELD OF THE INVENTION

The invention pertains to the use of Noble Gases for the treatment of pregnancy complications. More specifically, the invention pertains to modulation of inflammatory and/or immunomodulatory processes by administration of therapeutic gases comprising of at least one Noble Gas. More particularly, the invention pertains to reduction of recurrent spontaneous abortion (RSA) by administration of gas mixtures containing xenon.

BACKGROUND

Miscarriage is known to be one of the most common complications of pregnancy. The failure of pregnancy in the first trimester occurs in approximately 15-20% of pregnancies that have been documented by hCG testing, but the actual percentage of early pregnancy loss has not been precisely determined due to unconfirmed pregnancies [1]. RSA, is defined as the loss of three or more consecutive pregnancies, which is known to occur in 1-2% of couples attempting to conceive [2]. Medical causes of RSA usually are of immunological origin, in many cases associated with allogeneic immunity of the maternal immune system attacking paternal antigens, which is believed to account for 40-50% of miscarriages [3].

No method of treatment with definite curative effect is available heretofore. Currently, one widely used method for treating immunological RSA is lymphocyte immunotherapy. Immunotherapy of RSA has been applied both in China and other countries since Taylor and Faulk infused to a patient of unexplained RSA a suspension of mixed leukocytes derived from her spouse in 1981, which was subsequently confirmed in larger trials [4]. For this type of therapy, the immunogen is lymphocytes from the spouse in most cases. The immunotherapy includes isolating lymphocytes from the spouse's venous blood for intracutaneous injection. Alternatively, the condensed leucocytes or whole blood from the spouse can also be intravenously injected. Usually, the immunization is performed every 2 weeks for a total of 2 to 4 times before pregnancy and boosted 1 to 3 times after pregnancy. Twenty years after the application of lymphocyte immunotherapy for treating RSA, a great deal of studies from China and other countries have indicated that the therapeutic effect of this therapy is not definite and the therapy has some serious adverse side effects. Most literatures on immunotherapy of RSA from 1981 to 1994.9 had been reviewed. It was found that only one of the six studies that were worthy of analysis demonstrated the effectiveness of the immunotherapy. There was no statistically significant difference between the therapy group and the control group in the other studies. In addition, the lymphocyte immunotherapy has some serious adverse side effects such as erythrocyte sensitization, thrombocytopenia and intrauterine growth retardation of fetus etc. Some diseases transmitted by blood such as AIDS may be transferred from one individual to another due to the living cells with intact nuclear materials are used in lymphocyte therapy.

SUMMARY

Various aspects of the invention relating to the above are enumerated in the following paragraphs:

Aspect 1. A method of reducing risk of pregnancy complications comprising of administering a sufficient amount of a Noble Gas mixture capable of inhibiting anti-fetal associated maternal immune responses.

Aspect 2. The method of aspect 1, wherein said pregnancy complications are selected from a group comprising of: women at risk for recurrent spontaneous abortions (RSA), preterm birth, low birth weight, pre-eclampsia including hemolysis elevated liver enzymes low platelets (HELP), premature rupture of the membrane, Antepartum hemorrhage including placental abruption, chorioamnionitis, Intrauterine growth restriction, placenta pravaevia, sequalae of intraamniotic infection, and cerebral palsy.

Aspect 3. The method of aspect 2, wherein said risk of recurrent spontaneous abortion is defined as having one or more miscarriages in the first trimester of pregnancy.

Aspect 4. The method of aspect 2, wherein said risk of recurrent spontaneous abortion is defined as having a higher natural killer cell activity compared to an age-matched group of women with one or more successful pregnancies.

Aspect 5. The method of aspect 4, wherein said natural killer cell activity is defined as ability to induce death in vitro in a cell type susceptible to natural killer cell mediated killing.

Aspect 6. The method of aspect 2, wherein said risk of recurrent spontaneous abortion is defined as having a deficient T regulatory cell activity compared to an age-matched group of women with one or more successful pregnancies.

Aspect 7. The method of aspect 6, wherein said T regulatory cell activity is quantified by ability to inhibit a mixed lymphocyte reaction.

Aspect 8. The method of aspect 6, wherein said T regulatory cell activity is quantified by ability to inhibit proliferation of a lymphocyte after stimulation.

Aspect 9. The method of aspect 6, wherein said T regulatory cell activity is quantified by ability to inhibit cytokine production of a lymphocyte after stimulation.

Aspect 10. The method of aspect 9, wherein said cytokine is selected from a group comprising of: a) Interferon gamma; b) TNF-alpha; c) IL-12; d) IL-15; e) IL-17; f) IL-2 and g) IL-21.

Aspect 11. The method of 9, wherein said T regulatory cell possess ability to stimulate production of an anti-inflammatory cytokine selected from a group comprising of: a) IL-4; b) IL-10; c) IL-13; d) IL-20; e) TGF-beta.

Aspect 12. The method of aspect 2, wherein said risk of recurrent spontaneous abortion is defined as having a higher number of circulating natural killer cells as compared to a group of age-matched women with one or more successful pregnancies.

Aspect 13. The method of aspect 12, wherein said natural killer cells express a marker selected from a group comprising of: a) CD16; b) CD56; c) perforin; and d) CD94.

Aspect 14. The method of aspect 2, wherein said risk of recurrent spontaneous abortion is defined as having a lower number of circulating T regulatory cells as compared to a group of age-matched women with one or more successful pregnancies.

Aspect 15. The method of aspect 14, wherein said T regulatory cells express a marker selected from a group comprising of: a) FoxP3; b) TGF-beta; c) LAG; and d) CD73.

Aspect 16. The method of aspect 2 wherein said preterm birth is defined as birth before 37 weeks of gestation.

Aspect 17. The method of aspect 2, said risk of preterm birth is defined as possessing an increased vaginal or systemic concentrations of: a) sialidase; b) prolidase; c) glycosyltransferase types I, II and IV; d) monocyte chemotactic protein-1; e) matrix metalloproteases I, VIII and IX; f) IP-10; g) IL-6; h) IL-1 beta; i) TNF-alpha; j) fetal fibronectin and k) thrombin-antithrombin complex; 1) Salivary estriol as compared to a group of age-matched women having one or more successful pregnancies.

Aspect 18. The method of aspect 2, said risk of preterm birth is defined as possessing an decreased vaginal or systemic concentrations of: a) maternal serum placental leucine amniopeptidase (P-LAP); b) IL-10; c) insulin-like growth factor-binding protein-1 (IGBP-1); d) Pregnancy associated plasma protein-A (PAPP-A); e) Corticotropin-releasing hormone (CRH) as compared to a group of age-matched women having one or more successful pregnancies.

Aspect 19. The method of aspect 1, wherein said Noble Gas mixture is a mixture that contains oxygen and a proportion by volume of 20 to 70% of xenon.

Aspect 20. The method of aspect 19, wherein said proportion of xenon is between 22 and 60% by volume to oxygen.

Aspect 21. The method of aspect 20, wherein said proportion of xenon is between 25 and 60% by volume to oxygen.

Aspect 22. The method of aspect 1, wherein said noble gas containing mixture consists only of a) oxygen and xenon or b) air and xenon.

Aspect 23. The method of aspect 1, wherein said noble gas containing mixture also contains nitrogen, helium, Nitric Oxide, krypton, argon or neon.

Aspect 24. The method of aspect 1, wherein said noble gas containing mixture contains a proportion by volume of oxygen of between 15 and 25%.

Aspect 25. The method of aspect 1, wherein said noble gas containing mixture is supplied for inhalation from a pressurized container at a pressure greater than 2 bar.

Aspect 26. The method of aspect 1, wherein said noble gas containing mixture is administered intranasally.

Aspect 27. The method of aspect 1, wherein said noble gas containing mixture is administered through the use of a hyperbaric chamber.

Aspect 28. The method of aspect 27, wherein said hyperbaric chamber is pressurized to a pressure of no more than 3 atm (0.3 MPa).

Aspect 29. The method of aspect 28, wherein a noble gas is administered to the patient while the patient is in the hyperbaric environment.

Aspect 30. The method of aspect 1 wherein said noble gas is administered by inhalation or simulated inhalation.

Aspect 31. The method of aspect 1, wherein said noble gas is xenon, helium, or a mixture of xenon and helium.

Aspect 32. The method of aspect 1, wherein the noble gas is xenon or a mixture of xenon and helium, and the partial pressure of xenon is no more than about 0.8 atm (0.08 MPa).

Aspect 33. The method of aspect 1, wherein said noble gas is administered mixed with air, the air partial pressure being about 1 atm (0.1 MPa).

Aspect 34. The method of aspect 1, wherein said noble gas is administered as part of a gas mixture comprising oxygen, the nitrogen partial pressure in the mixture being equal to or less than about 0.8 atm (0.08 MPa). Aspect 35. The method of aspect 34, wherein said gas mixture is essentially free of nitrogen.

Aspect 36. The method of aspect 35, wherein the oxygen partial pressure is about 0.2 atm (0.02 MPa).

DETAILED DESCRIPTION OF THE INVENTION

The invention provides for modification of immunological/inflammatory responses through administration of Noble Gas containing mixtures in a manner so as to reduce the risk of pregnancy complications. In one particular embodiment, said pregnancy complications include disorders associated with pregnancy loss. In one embodiment, recurrent spontaneous abortions are a complication of pregnancy that is treated by the current invention. Support for RSA being immunologically mediated resides from studies showing aspects of Th1/Th17 immunity correlated with RSA. For example, Gao and Wang compared 30 control pregnancies with 30 pregnancies with a history of RSA. They found that there was a higher proportion of CD4(+) T cells and CD16(+)CD56(+) NK cells and a lower number of CD8(+) T cells in the decidual tissue of RSA patients compared to normal controls. In addition, the number of T helper type 1 (Th1) cells and the Th1/Th2 ratio were higher in RSA patients compared to normal pregnant controls. The authors concluded that the proportion of local T lymphocyte subsets, NK and Th1 cells, in the maternal-fetal interface correlates to occurrence of RSA [5]. These data would conceptually be aligned with the role of NK cells, which are known to produce cytokines that are cytotoxic, such as TNF-alpha, as well as anti-angiogenic cytokines such as IFN-gamma [6-9]. The localized induction of cytotoxicity, as well as blockade of angiogenesis at the fetal-maternal interface would cause pregnancy loss by disruption of the delicate process of neovascularization which is essential for successful pregnancy [10-16]. In one embodiment of the invention concentration of said Noble Gas mixtures is adjusted in a patient at risk of RSA by assessing ex vivo production of TNF-alpha with the attempt to modulate dosage of said Noble Gas with the goal of reducing TNF-alpha production in circulation of said woman attempting to undergo pregnancy. Numerous means of assessing TNF-alpha production are known and include ELISA, ELISPOT, intracellular flow cytometry and ex vivo activation of monocytes extracted from said patient. In one particular embodiment of the invention, a mixture of about 30% xenon and 70% air is administered in a volume of 2-10 liters once to three times per week for a total of 1-5 weeks. One of skill in the art will understand that these concentrations may be modified by personalization of treatment regimen based on cytokine production.

Th17 cells are associated with stimulation of tissue damage, in part through the direct production of TNF-alpha, as well as stimulation of monocytes to produce this cytotoxic cytokine [17-26]. Liu et al. reported that the proportion of Th17 cells and IL-17A concentrations was both significantly higher in patients with RSA than in normal early pregnant (NEP) and non-pregnant (NP) patients, Treg frequencies were significantly lower in patients with RSA than in NEP patients, and the ratio of Th17 to Treg was significantly higher in the RSA group than in the other two. Additionally, the percentage of IL-17A cells in deciduas was significantly higher in patients with RSA than in NEP patients [27].

Supporting the role of TNF-alpha in RSA, Zhang et al performed a meta-analysis of observational studies to detect the association between RSM and TNF-α levels. By searching PubMed, EMBase, ScienceDirect, Web of Science, and Chinese databases (including: Wanfang Data, CNKI, and VIP databases) for articles published up to 2014, they identified 151 studies, of which 11 case-control studies with 1371 patients were analyzed. Overall, baseline TNF-α levels were higher in RSA patients than in control pregnancies. The standardized mean difference of the TNF-α levels of the RSA patients was 2.82 units (95% confidence interval 1.57-4.06) and the overall effect z-score was 4.42 (P<0.0001). The heterogeneity test revealed significant differences among individual studies (P=0.000, I(2)=98.7%). Serum TNF-α levels were significantly increased in patients relative to those in controls [28]. The results of this study suggest that in RSA the level of TNF-alpha is not just localized to the maternal-fetal interface, but is so elevated that it reaches levels which can be detected systemically.

TNF-alpha, as well as Th1 and Th17 cells are inhibited by T regulatory (Treg) cells [29-33]. Treg cells are typically involved in maintaining self-tolerance, a process that protects from autoimmune conditions, as well as maintains viability of transplanted allografts [34-37]. In line with the notion of deregulated TNF-alpha and Th1/Th17 elevation, studies have found reduction of Treg cells and Treg activity in RSA patients. Zhang et al demonstrated that proportions of CD4(+)FOXP3(+) T cells and CCR6(+)CD4(+)FOXP3(+) T cells were lower in RSA patients than in healthy controls for both systemic peripheral blood (PB) lymphocytes and at the fetal-maternal interface as assessed by decidual samples (P<0.05). Expression levels of FOXP3 and CCR6 mRNA were lower in RSA patients than in control subjects for PB and decidual samples (P<0.05). CCL20 protein levels were lower in RSA patients than in controls (P<0.05). An effect of Treg migration was significantly blocked (by 89.13%) using a neutralizing anti-CCL20 antibody in vitro. Furthermore, CCL20-stimulated Tregs exhibited a 3.21-fold increase in migration and this was blocked using a neutralizing anti-CCL20 antibody. IL-10 concentration in culture supernatants of CD4(+)CD25(+)CD127(dim/−) Tregs of RSA patients was significantly lower than that in controls. Anti-CCL20 antibody inhibited IL-10 and IL-4 expression but increased IFN-r and IL-17 levels when there was cell-cell contact between PB CD4(+)CD25(+) T cells and CD4(+)CD25(−) T cells [38].

Mei et al observed similar results in the reduction of Treg cells in RSA patients. Specifically, they performed a comparison between 125 RSA patients, 35 normal early pregnant women, and 28 normal nonpregnant women. A comparison was made between flow cytometric analysis of cellular phenotype by assessing CD4+CD25high T cells, as well as functional properties by quantifying FOXP3 expression in peripheral blood and decidua. They found that in peripheral blood, statistically significantly higher proportions of CD4+CD25high T cells and FOXP3 expression were observed in normal early pregnant women compared with normal nonpregnant women and RSA patients; a statistically significantly lower proportion of CD4+CD25high T cells was observed in nonpregnant RSA patients compared with RSA patients who had early miscarriages and normal nonpregnant women. In the decidua, statistically significantly lower proportions of CD4+CD25high T cells and FOXP3 expression were found in RSA patients with early miscarriages compared with normal early pregnant women. The authors concluded that the CD4+CD25high T cells play an important role in maintaining a normal pregnancy and that the reduction in CD4+CD25high T cells is involved in the pathogenesis of RSA, and is correlated with lower FOXP3 expression [39].

Thus, in one embodiment of the invention, therapeutic Noble Gas compositions are administered in a manner to alter immunological factors in the body. Specifically, the invention teaches that various concentrations of xenon gas, when delivered into circulation, either by inhalation [40-42], or administration of echogenic xenon liposomes [43, 44], can be utilized to induce a T regulatory cell phenotype and suppression of Th17 or other abortogenic cells. The use of xenon has been reviewed by numerous authors in the art, which provide guidance as to details of administration [45-47]. Importantly, the new and non-obvious aspect of the current invention is that xenon, as well as other Noble gases, are capable of inducing immune modulation to inhibit pregnancy complications.

Examples of gases or gas mixtures employed as medicament for radiation protection: 1.) 100% by volume xenon; 2.) 70% by volume xenon/30% by volume oxygen; 3.) 65% by volume xenon/30% by volume oxygen/5% by volume nitrogen; 4.) 65% by volume xenon/35% by volume oxygen; 5.) 60% by volume xenon/30% by volume oxygen/10% by volume nitrogen; 6.) 60% by volume xenon/35% by volume oxygen/5% by volume nitrogen; 7.) 60% by volume xenon/40% by volume oxygen; 8.) 55% by volume xenon/25% by volume oxygen/20% by volume nitrogen; 9.) 55% by volume xenon/30% by volume oxygen/15% by volume nitrogen; 10.) 55% by volume xenon/35% by volume oxygen/10% by volume nitrogen; 11.) 55% by volume xenon/40% by volume oxygen/5% by volume nitrogen; 12.) 55% by volume xenon/45% by volume oxygen; 13.) 50% by volume xenon/50% by volume oxygen; 14.) 50% by volume xenon/45% by volume oxygen/5% by volume nitrogen; 15.) 50% by volume xenon/40% by volume oxygen/10% by volume nitrogen; 16.) 50% by volume xenon/30% by volume oxygen/20% by volume nitrogen; 17.) 50% by volume xenon/25% by volume oxygen/25% by volume nitrogen; 18.) 45% by volume xenon/55% by volume oxygen; 19.) 45% by volume xenon/50% by volume oxygen/5% by volume nitrogen; 20.) 45% by volume xenon/45% by volume oxygen/10% by volume nitrogen; 21.) 45% by volume xenon/40% by volume oxygen/15% by volume nitrogen; 22.) 45% by volume xenon/35% by volume oxygen/20% by volume nitrogen; 23.) 45% by volume xenon/30% by volume oxygen/25% by volume nitrogen; 24.) 45% by volume xenon/30% by volume oxygen/25% by volume nitrogen; 25.) 40% by volume xenon/30% by volume oxygen/30% by volume nitrogen; 26.) 40% by volume xenon/50% by volume oxygen/10% by volume nitrogen; 27.) 35% by volume xenon/25% by volume oxygen/40% by volume nitrogen; 28.) 35% by volume xenon/65% by volume oxygen; 29.) 30% by volume xenon/70% by volume oxygen; 30.) 30% by volume xenon/50% by volume oxygen/20% by volume nitrogen; 31.) 30% by volume xenon/30% by volume oxygen/40% by volume nitrogen; 32.) 20% by volume xenon/80% by volume oxygen; 33.) 20% by volume xenon/30% by volume oxygen/50% by volume nitrogen; 34.) 15% by volume xenon/30% by volume oxygen/55% by volume nitrogen; 35.) 15% by volume xenon/50% by volume oxygen/35% by volume nitrogen; 36.) 10% by volume xenon/90% by volume oxygen; 37.) 10% by volume xenon/50% by volume oxygen/40% by volume nitrogen; 38.) 10% by volume xenon/30% by volume oxygen/60% by volume nitrogen; 39.) 10% by volume xenon/25% by volume oxygen/65% by volume nitrogen; 40.) 5% by volume xenon/25% by volume oxygen/70% by volume nitrogen; 41.) 5% by volume xenon/

30% by volume oxygen/65% by volume nitrogen; 42.) 5% by volume xenon/50% by volume oxygen/45% by volume nitrogen; 43.) 5% by volume xenon/30% by volume oxygen/65% by volume nitrogen; 44.) 5% by volume xenon/95% by volume oxygen; 45.) 1% by volume xenon/99% by volume oxygen; 46.) 1% by volume xenon/30% by volume oxygen/69% by volume nitrogen; 47.) 1% by volume xenon/25% by volume oxygen/74% by volume nitrogen.

The provided invention for fetal protection and the indications mentioned, is for example a gas mixture which comprises from 1 to 80% by volume (based on standard conditions, i.e. 20.degree. C., 1 bar absolute) xenon (e.g. remainder oxygen). The medicament which is administered to the patient comprises xenon in pharmacologically or therapeutically effective amount, in particular in subanesthetically or anesthetically effective amount. A medicament with xenon in subanesthetically effective amount is advantageous. Subanesthetically effective (subanesthetic) amounts of xenon mean those amounts or concentrations of xenon which are insufficient for general anesthesia. These are in general amounts of up to 70% by volume xenon, preferably up to 65% by volume, particularly preferably up to 60% by volume, in particular up to 50% by volume xenon. Pure xenon is accordingly metered into the patient's respiratory gas in the stated concentrations. This means that the respiratory gas supplied to the patient comprises for example from 5 to 60% by volume, 5 to 50% by volume, 5 to 40% by volume, 5 to 30% by volume or 5 to 20% by volume xenon. In special cases, e.g. for prophylaxis, especially during prolonged ventilation, a dosage of xenon in the respiratory gas with a low concentration, for example 1 to 35% by volume, 5 to 25% by volume or 5 to 20% by volume xenon in the respiratory gas, may be advantageous. The medicaments, in particular gaseous medicaments, preferably comprise besides xenon one or more gases or substances which are gaseous at body temperature under atmospheric pressure. Examples of gas mixtures which can be used are xenon-oxygen gas mixtures or gas mixtures of xenon and one or more inert gases such as nitrogen or a rare gas or xenon-oxygen inert gas mixtures. Admixture of a gas to the xenon may be very advantageous if it is intended to introduce little xenon into the body.

REFERENCES

1. Carrington, B., G. Sacks, and L. Regan, *Recurrent miscarriage: pathophysiology and outcome.* Curr Opin Obstet Gynecol, 2005. 17(6): p. 591-7.
2. Wong, L. F., T. F. Porter, and J. R. Scott, *Immunotherapy for recurrent miscarriage.* Cochrane Database Syst Rev, 2014(10): p. CD000112.
3. Imam, S. N., et al., *Idiopathic recurrent pregnancy loss: role of paternal factors; a pilot study.* J Reprod Infertil, 2011. 12(4): p. 267-76.
4. Taylor, C. G., W. P. Faulk, and J. A. McIntyre, *Prevention of recurrent spontaneous abortions by leukocyte transfusions.* J R Soc Med, 1985. 78(8): p. 623-7.
5. Gao, Y. and P. L. Wang, *Increased CD56(+) NK cells and enhanced Th1 responses in human unexplained recurrent spontaneous abortion.* Genet Mol Res, 2015. 14(4): p. 18103-9.
6. Sun, T., et al., *Inhibition of tumor angiogenesis by interferon-gamma by suppression of tumor-associated macrophage differentiation.* Oncol Res, 2014. 21(5): p. 227-35.
7. Maheshwari, R. K., et al., *Differential effects of interferon gamma and alpha on in vitro model of angiogenesis.* J Cell Physiol, 1991. 146(1): p. 164-9.
8. Battle, T. E., R. A. Lynch, and D. A. Frank, *Signal transducer and activator of transcription 1 activation in endothelial cells is a negative regulator of angiogenesis.* Cancer Res, 2006. 66(7): p. 3649-57.
9. Kishuku, M., et al., *Expression of soluble vascular endothelial growth factor receptor-1 in human monocyte-derived mature dendritic cells contributes to their anti-angiogenic property.* J Immunol, 2009. 183(12): p. 8176-85.
10. Wang, L., et al., *Insights into the mechanism of CXCL12-mediated signaling in trophoblast functions and placental angiogenesis.* Acta Biochim Biophys Sin (Shanghai), 2015. 47(9): p. 663-72.
11. Zimna, A. and M. Kurpisz, *Hypoxia-Inducible Factor-1 in Physiological and Pathophysiological Angiogenesis: Applications and Therapies.* Biomed Res Int, 2015. 2015: p. 549412.
12. Jardim, L. L., et al., *Is the imbalance between pro-angiogenic and anti-angiogenic factors associated with preeclampsia?* Clin Chim Acta, 2015. 447: p. 34-8.
13. Ratsep, M. T., et al., *Uterine natural killer cells: supervisors of vasculature construction in early decidua basalis.* Reproduction, 2015. 149(2): p. R91-102.
14. Kwak-Kim, J., et al., *Immunological modes of pregnancy loss: inflammation, immune effectors, and stress.* Am J Reprod Immunol, 2014. 72(2): p. 129-40.
15. Chen, D. B. and J. Zheng, *Regulation of placental angiogenesis.* Microcirculation, 2014. 21(1): p. 15-25.
16. Shibuya, M., *Vascular endothelial growth factor and its receptor system: physiological functions in angiogenesis and pathological roles in various diseases.* J Biochem, 2013. 153(1): p. 13-9.
17. Shabgah, A. G., E. Fattahi, and F. Z. Shahneh, *Interleukin-17 in human inflammatory diseases.* Postepy Dermatol Alergol, 2014. 31(4): p. 256-61.
18. Cosmi, L., et al., *Th17 and non-classic Th1 cells in chronic inflammatory disorders: two sides of the same coin.* Int Arch Allergy Immunol, 2014. 164(3): p. 171-7.
19. Annunziato, F., et al., *Reasons for rarity of Th17 cells in inflammatory sites of human disorders.* Semin Immunol, 2013. 25(4): p. 299-304.
20. Qu, N., et al., *Pivotal roles of T-helper 17-related cytokines, IL-17, IL-22, and IL-23, in inflammatory diseases.* Clin Dev Immunol, 2013. 2013: p. 968549.
21. Osnes, L. T., et al., *Assessment of intracellular cytokines and regulatory cells in patients with autoimmune diseases and primary immunodeficiencies—novel tool for diagnostics and patient follow-up.* Autoimmun Rev, 2013. 12(10): p. 967-71.
22. Siakavellas, S. I. and G. Bamias, *Role of the IL-23/IL-17 axis in Crohn's disease.* Discov Med, 2012. 14(77): p. 253-62.
23. Zhu, S. and Y. Qian, *IL-17/IL-17 receptor system in autoimmune disease: mechanisms and therapeutic potential.* Clin Sci (Lond), 2012. 122(11): p. 487-511.
24. Ferraccioli, G. and G. Zizzo, *The potential role of Th17 in mediating the transition from acute to chronic autoimmune inflammation: rheumatoid arthritis as a model.* Discov Med, 2011. 11(60): p. 413-24.
25. Jadidi-Niaragh, F. and A. Mirshafiey, *Th17 cell, the new player of neuroinflammatory process in multiple sclerosis.* Scand J Immunol, 2011. 74(1): p. 1-13.

26. Mills, K. H., *Induction, function and regulation of IL-17-producing T cells*. Eur J Immunol, 2008. 38(10): p. 2636-49.
27. Liu, Y. S., et al., *Study on the relationship between Th17 cells and unexplained recurrent spontaneous abortion*. Am J Reprod Immunol, 2011. 65(5): p. 503-11.
28. Zhang, C., et al., *Association between Serum TNF-alpha Levels and Recurrent Spontaneous Miscarriage: A Meta-analysis*. Am J Reprod Immunol, 2016. 75(2): p. 86-93.
29. Hirahara, K. and T. Nakayama, *CD4+ T-cell subsets in inflammatory diseases: beyond the Th1/Th2 paradigm*. Int Immunol, 2016. 28(4): p. 163-71.
30. Kumar, P. and G. Subramaniyam, *Molecular underpinnings of Th17 immune-regulation and their implications in autoimmune diabetes*. Cytokine, 2015. 71(2): p. 366-76.
31. Raphael, I., et al., *T cell subsets and their signature cytokines in autoimmune and inflammatory diseases*. Cytokine, 2015. 74(1): p. 5-17.
32. Duan, M. C., et al., *The Treg/Th17 paradigm in lung cancer*. J Immunol Res, 2014. 2014: p. 730380.
33. Buc, M., *Role of regulatory T cells in pathogenesis and biological therapy of multiple sclerosis*. Mediators Inflamm, 2013. 2013: p. 963748.
34. Taflin, C., et al., *Regulation of the CD4+ T cell alloimmune response by endothelial cells*. Hum Immunol, 2012. 73(12): p. 1269-74.
35. Hilbrands, R., et al., *Induced Foxp3(+) T Cells Colonizing Tolerated Allografts Exhibit the Hypomethylation Pattern Typical of Mature Regulatory T Cells*. Front Immunol, 2016. 7: p. 124.
36. Tang, J., et al., *IL-25 promotes the function of CD4+ CD25+T regulatory cells and prolongs skin-graft survival in murine models*. Int Immunopharmacol, 2015. 28(2): p. 931-7.
37. Zhou, Y., et al., *The roles of T helper type 17/regulatory T cells in acute rejection after liver transplantation in rats*. Transplantation, 2015. 99(6): p. 1126-31.
38. Zhang, X. X., X. M. Kang, and A. M. Zhao, *Regulation of CD4(+)FOXP3(+) T cells by CCL20/CCR6 axis in early unexplained recurrent miscarriage patients*. Genet Mol Res, 2015. 14(3): p. 9145-54.
39. Mei, S., et al., *Changes of CD4+CD25high regulatory T cells and FOXP3 expression in unexplained recurrent spontaneous abortion patients*. Fertil Steril, 2010. 94(6): p. 2244-7.
40. Laitio, R., et al., *Effect of Inhaled Xenon on Cerebral White Matter Damage in Comatose Survivors of Out-of-Hospital Cardiac Arrest: A Randomized Clinical Trial*. JAMA, 2016. 315(11): p. 1120-8.
41. Arola, O. J., et al., *Feasibility and cardiac safety of inhaled xenon in combination with therapeutic hypothermia following out-of-hospital cardiac arrest*. Crit Care Med, 2013. 41(9): p. 2116-24.
42. Azzopardi, D., et al., *Moderate hypothermia within 6 h of birth plus inhaled xenon versus moderate hypothermia alone after birth asphyxia (TOBY-Xe): a proof-of-concept, open-label, randomised controlled trial*. Lancet Neurol, 2015.
43. Britton, G. L., et al., *In vivo therapeutic gas delivery for neuroprotection with echogenic liposomes*. Circulation, 2010. 122(16): p. 1578-87.
44. Peng, T., et al., *Therapeutic time window and dose dependence of xenon delivered via echogenic liposomes for neuroprotection in stroke*. CNS Neurosci Ther, 2013. 19(10): p. 773-84.
45. Maze, M., *Preclinical neuroprotective actions of xenon and possible implications for human therapeutics: a narrative review*. Can J Anaesth, 2016. 63(2): p. 212-26.
46. Sanders, R. D. and M. Maze, *Xenon: from stranger to guardian*. Curr Opin Anaesthesiol, 2005. 18(4): p. 405-11.
47. Esencan, E., et al., *XENON in medical area: emphasis on neuroprotection in hypoxia and anesthesia*. Med Gas Res, 2013. 3(1): p. 4.

The invention claimed is:

1. A method of reducing risk of pregnancy complications in a pregnant woman at risk for recurrent spontaneous abortions (RSA), comprising: administering to said pregnant women a sufficient amount of a Noble Gas mixture capable of inhibiting anti-fetal associated maternal immune responses,
    wherein, said Noble Gas containing mixture consisting essentially only of a) oxygen and xenon or b) air and xenon,
    and wherein said risk of recurrent spontaneous abortion is defined by the criteria selected from the group consisting of: a) having a higher number of circulating natural killer cells as compared to a group of age-matched women with one or more successful pregnancies, and b) having a lower number of circulating T regulatory cells as compared to a group of age-matched women with one or more successful pregnancies.

2. The method of claim 1, wherein said Noble Gas mixture is a mixture that contains oxygen and a proportion by volume of 20 to 70% of xenon.

3. The method of claim 2, wherein said proportion of xenon is between 22 and 60% by volume to oxygen.

4. The method of claim 3, wherein said proportion of xenon is between 25 and 60% by volume to oxygen.

5. The method of claim 1, wherein said noble gas containing mixture contains a proportion by volume of oxygen of between 15 and 25%.

6. The method of claim 1, wherein said noble gas containing mixture is supplied for inhalation from a pressurized container at a pressure greater than 2 bar.

7. The method of claim 1, wherein said noble gas containing mixture is administered intranasally.

8. The method of claim 1, wherein said noble gas containing mixture is administered through the use of a hyperbaric chamber.

9. The method of claim 8, wherein said hyperbaric chamber is pressurized to a pressure of no more than 3 atm (0.3 MPa).

10. A method of reducing risk of pregnancy complications in a pregnant woman comprising: administering to said pregnant women a sufficient amount of a Noble Gas mixture capable of inhibiting anti-fetal associated maternal immune responses,
    wherein, said Noble Gas containing mixture consisting essentially only of a) oxygen and xenon or b) air and xenon, and
    wherein said Noble Gas mixture is inhaled by said pregnant woman from a pressurized container at a pressure greater than 2 bar.

11. A method of reducing risk of pregnancy complications in a pregnant woman comprising: administering to said pregnant women a sufficient amount of a Noble Gas mixture capable of inhibiting anti-fetal associated maternal immune responses,
    wherein, said Noble Gas containing mixture consisting essentially only of a) oxygen and xenon or b) air and xenon, and wherein said Noble Gas mixture is administered to said pregnant woman through the use of a hyperbaric chamber.

* * * * *